(12) United States Patent
McPhail et al.

(10) Patent No.: US 8,034,780 B2
(45) Date of Patent: Oct. 11, 2011

(54) ISOLATION, PURIFICATION, AND STRUCTURE ELUCIDATION OF THE ANTIPROLIFERATIVE COMPOUND COIBAMIDE A

(76) Inventors: Kerry Leigh McPhail, Corvallis, OR (US); Rebecca Ann Medina, Corvallis, OR (US); William Henry Gerwick, La Jolla, CA (US); Douglas Eugene Goeger, Albany, OR (US); Todd Leo Capeon, San Diego, CA (US)

( * ) Notice: Subject to any disclaimer, the term of this patent is extended or adjusted under 35 U.S.C. 154(b) by 612 days.

(21) Appl. No.: 12/174,216

(22) Filed: Jul. 16, 2008

(65) Prior Publication Data
US 2009/0023642 A1 Jan. 22, 2009

Related U.S. Application Data

(60) Provisional application No. 60/969,793, filed on Jul. 16, 2007.

(51) Int. Cl.
*A61K 38/12* (2006.01)
(52) U.S. Cl. .................................. 514/19.2; 514/21.1
(58) Field of Classification Search .................... None
See application file for complete search history.

(56) References Cited

OTHER PUBLICATIONS

Mezo et al. "Conformational study of linear and cyclic peptides corresponding to the 276-284 epitope region of HSV gD-1" Biophysical Chemistry (2003), 103(1), 51-65.*

* cited by examiner

*Primary Examiner* — Christina Bradley
(74) *Attorney, Agent, or Firm* — Dann, Dorfman, Herrell & Skillman; Robert C. Netter, Jr.

(57) ABSTRACT

Novel antiproliferative compounds, compositions comprising the same, and methods of use thereof are disclosed.

4 Claims, 7 Drawing Sheets

A

B

A

B

R = CH₃, benzyl or other protecting group
R₁ = Ns, Boc or Fmoc
R₂ = TBDMS or other protecting group

C

US 8,034,780 B2

ISOLATION, PURIFICATION, AND STRUCTURE ELUCIDATION OF THE ANTIPROLIFERATIVE COMPOUND COIBAMIDE A

This application claims priority under 35 U.S.C. §119(e) to U.S. Provisional Patent Application No. 60/959,793, filed on Jul. 16, 2007. The foregoing application is incorporated by reference herein.

This invention was made with government support under grant number 1U01 TW006634-01 and grant number 5 R01 GM063554 awarded by the National Institutes of Health. The government has certain rights in the invention.

FIELD OF THE INVENTION

This invention relates to the treatment of cancer. Specifically, the invention relates to the isolation, purification, and structure elucidation of the novel antiproliferative compound Coibamide A.

BACKGROUND OF THE INVENTION

Cancer is a group of diseases characterized by uncontrolled proliferation of aberrant, undifferentiated cells (tumor formation) which may spread throughout the body to invade other tissues (metastasis). Mutations in oncogenes, tumor-suppressor genes and stability genes may contribute to the development of a cancer by promoting cell division and growth and inhibiting cell death or cell-cycle arrest (Vogelstein et al. (2004) Nature Med., 10:789-799). No single gene defect is the sole cause of any cancer, necessitating a detailed understanding of the biology of each different cancer type for the development of effective, cancer-specific treatments.

Cancer treatment options were limited to surgery to remove the tumor mass before 1950, while ionizing radiation therapy was introduced in the 1960's. However, neither of these treatments can reach every organ of the body to eradicate metastatic cancers. Therefore, chemotherapy has become a focus in cancer treatment (Chabner et al. (2005) Nat. Rev. Cancer, 5:65-72). Natural products are the ultimate source of 62-67% of the agents in clinical trial for the treatment of cancer (Newman et al. (2007) J. Nat. Prod., 70:461-477). At the end of 2006, there were 185 anticancer drugs available in the West and Japan, of which only 24% (42) were wholly synthetic agents. Of the remaining 76%, 25 (14%) were unmodified natural products, 48 (28%) were modified natural products, 40 (23%) were based on a natural product pharmacophore or mimic natural products and 20 (11%) were "biological" (e.g., proteins) and vaccines (Newman et al. (2007) J. Nat. Prod., 70:461-477). These compounds used alone or in combination with surgery or radiation have had varied success as is reflected in the comparable USA cancer death rates for 1950 and 2005, which is in sharp contrast to the dramatically reduced 2005 death rates attributed to heart diseases, cerebrovascular diseases and pneumonia/influenza (Amer. Cancer Soc. (2008) Cancer Statistics www.cancer.org/docroot/PRO/content/PRO_1_1_Cancer_Statistics_2008_Presentation.asp). Even in the USA, approximately only 50% of all individuals afflicted with any cancer attain long term survival (Brenner, H. (2002) The Lancet, 360: 9340). Accordingly, there is a need in the art to isolate and purify novel, potent cancer chemotherapeutic agents.

Two modified natural products were recently approved (2007) as cancer treatments: ixabepilone (analog of *Myxobacterium*-derived epothilone B, Ixempra®) for advanced metastatic breast cancer (Moulder (2008) Future Oncology, 4:333-340) and temsirolimus (derivative of rapamycin from *Streptomyces hygroscopicus*, Torisel®) for advanced renal cancer (Simpson and Curran (2008) Drugs, 68:631-638). Examples of natural products or natural product derivatives in current cancer clinical trials (www.cancer.gov/clinicaltrials) with the National Cancer Institute are FR901228 (from *Chromobacterium violaceum*), bryostatin-1 (from marine bryozoan *Bugula neritina*) and 17-AAG (analog of geldanamycin from *Streptomyces hygroscopicus*). Marine organisms continue to yield a diverse array of biologically active molecules, a remarkable number of which are peptide-based cancer cell toxins of putative microbial symbiont biogenesis (Simmons et al. (2008) Proc. Natl. Acad. Sci., 105:4587-4594). Development of these as anticancer drugs has met with some success (Rawat et al. (2006) Med. Chem., 6:33-40). Indeed, there are as many as 50 marine-derived natural products or derivatives in clinical and preclinical trials (Newman et al. (2004) J. Nat. Prod., 67:1216-1238). Ecteinascidin 743 (from the tunicate *Ecteinascidia turbinata*) and Neovastat (from a shark) have progressed to phase III trials where they are being used to treat larger numbers of people. Ecteinascidin 743 (YONDELIS®, trabectedin) is a tetrahydroisoquinolone alkaloid that binds DNA by a novel mechanism, and is being developed by the Spanish company PharmaMar for the treatment of soft tissue sarcomas (Fayette et al. (2006) Curr. Opin. Oncol., 18:347-353). Neovastat (AE941) is an extract of shark cartilage with potent anti-angiogenic activity in phase III trials for lung and renal carcinoma (Gingras et al. (2002) Anti-Cancer Drugs, 14:91-96), and has recently been elucidated as immunoglobulin kappa light chain (28 kDa protein; Boivin et al. (2004) Arch. Biochem. Biophys., 431:197-206). Further, ascidian-derived dihydrodidemnin B (Aplidin®) has orphan drug status for the treatment of multiple myeloma and acute lymphoblastic leukemia; the green algal isolate kahalalide F has also reached phase II clinical trials.

The Cyanobacteria (blue-green algae) are an ancient group of opportunistic, often toxic colonial organisms, which commonly show spatial and temporal variation in biomass and may indicate shallow reef damage or stagnant waters. The majority of marine cyanobacterial metabolites reported to date has been isolated from the genus *Lyngbya* and are products of mixed peptide and ketide biosynthesis. This structural class has been a rich source of lead compounds in the development of treatments for cancer (Gerwick, et al. (2001) In: Alkaloids: Chemistry and Biology. Cordell, Ga. (Ed). Academic Press: N.Y. Vol. 57, pp 75-184; Tan, L. T. (2007) Phytochem., 68:954-979), and includes the antimitotic agents curacin A, dolastatins 10 and 15, and cryptophycins (Newman et al. (2004) J. Nat. Prod., 67:1216-1238). Synthetic analogs of curacin A and dolastatins 10 and 15 are in preclinical and clinical trials, respectively. Indeed, TZT-1027, a synthetic analogue of the cyanobacterial metabolite dolastatin 10, has reached phase II clinical trials. The high degree of N-methylation of many of these cyanobacterial peptides may improve their suitability as a drug since N-methylation has been shown to improve pharmacological parameters such as lipophilicity, proteolytic stability, and duration of action, properties for which regular peptides are notoriously poor and which limits their bioavailability (Loffert, A. J. (2002) Pept. Sci., 8:1-7; Morishita et al. (2006) Drug Discovery Today, 11:905-910).

SUMMARY OF THE INVENTION

In accordance with one aspect of the invention, compounds having antiproliferative activity are provided. In a particular embodiment, the compounds are compounds of formula I, variants or derivatives thereof, or a pharmaceutically acceptable salt thereof. In yet another embodiment, the compound is Coibamide A.

In accordance with another aspect of the invention, compositions comprising at least one compound of the instant invention and at least one pharmaceutically acceptable carrier are provided. In a particular embodiment, the composition further comprises at least one chemotherapeutic agent.

In still another embodiment, methods for the treatment of cancer in a patient comprising administering at least one composition of the instant invention are provided. In a particular embodiment, the method further comprises the administration of at least one chemotherapeutic agent.

purified from a Panamanian marine cyanobacterium tentatively assigned to the genus *Leptolyngbya*. The structure of the novel compound was elucidated using NMR spectroscopy and mass spectrometry. In addition, its biological activity was tested against various cancer cell lines as described hereinbelow.

According to one embodiment, compounds of the instant invention are encompassed by the chemical structure outlined in formula (I). The compounds may comprise the D and L amino acid configurations independently at all amino acid positions ($R_3$, $R_5$, $R_7$, $R_9$, $R_{11}$, $R_{13}$, $R_{15}$, $R_{17}$, $R_{19}$, $R_{21}$, $R_{23}$ are the amino acid side chains). Formula I also encompasses all chiral variants (e.g., enatiomers such as R or S). Compositions comprising the compounds of the instant invention may comprise racemic mixtures, pure enantiomers, and/or enantiomerically enriched compounds. As indicated below, $R_4$ is selected from the group consisting of O, NH, S, and NMe and $R_{12}$ is selected from the group consisting of O, N, and S. In another embodiment, $R_1$, $R_2$, $R_6$, $R_8$, $R_{10}$, $R_{14}$, $R_{16}$, $R_{18}$, $R_{20}$, $R_{22}$ and $R_{24}$ are independently H or Me. The instant invention also encompasses pharmaceutically acceptable salts of formula I.

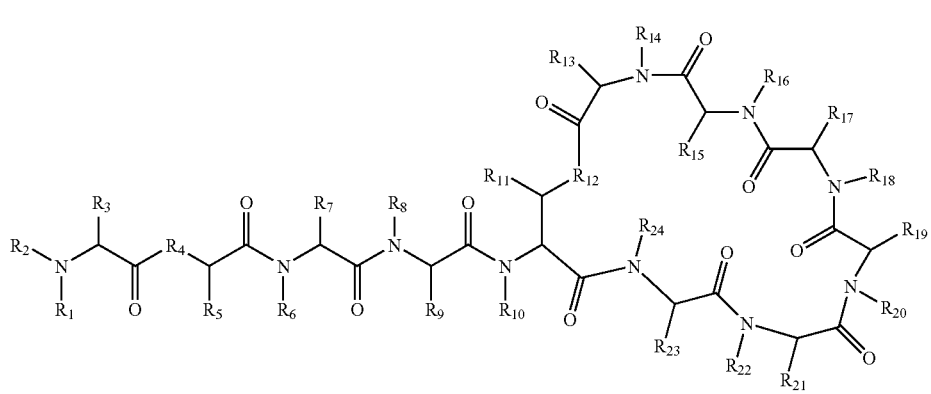

(I)

Figure 3A:
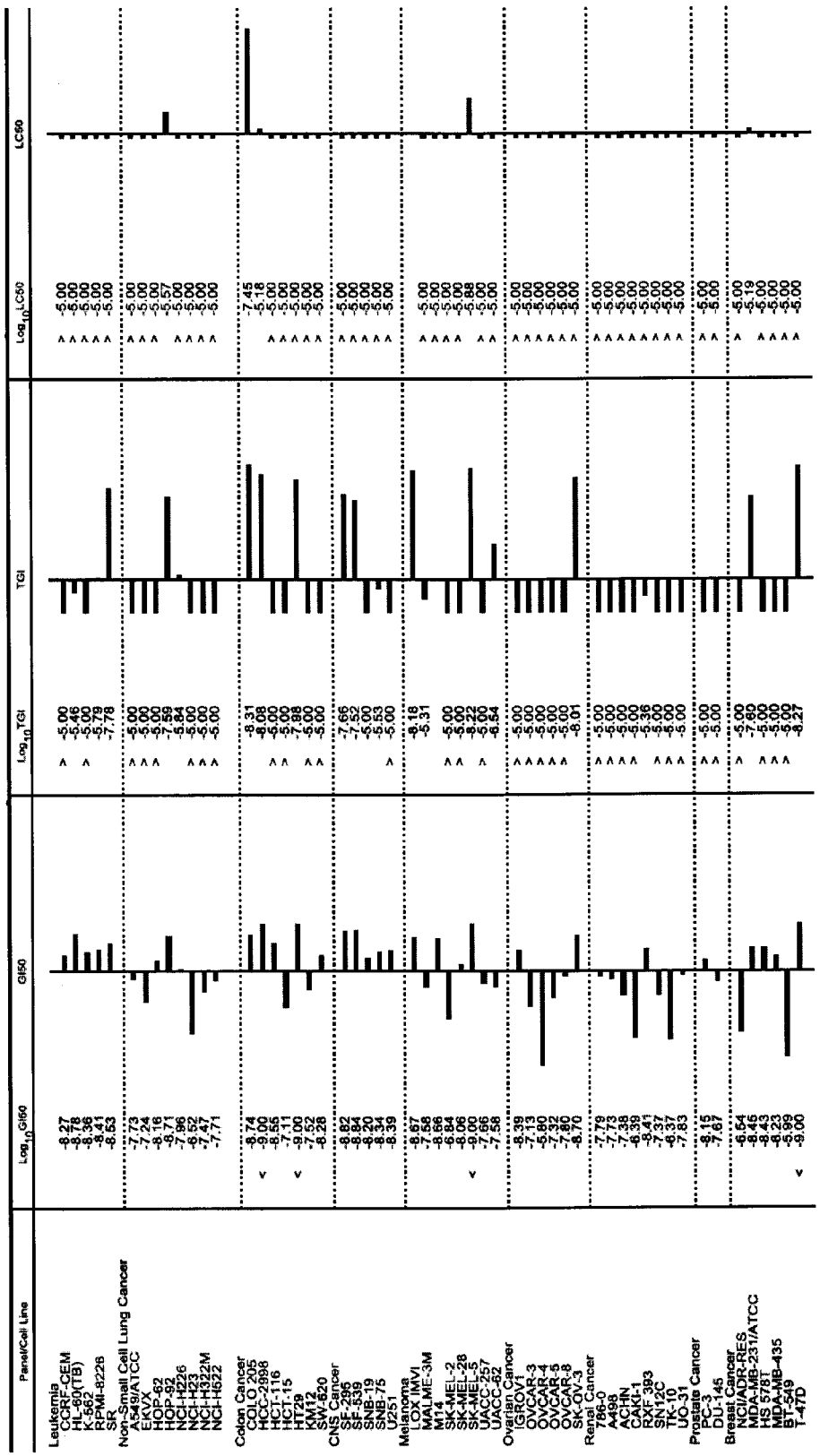
Figure 3B:
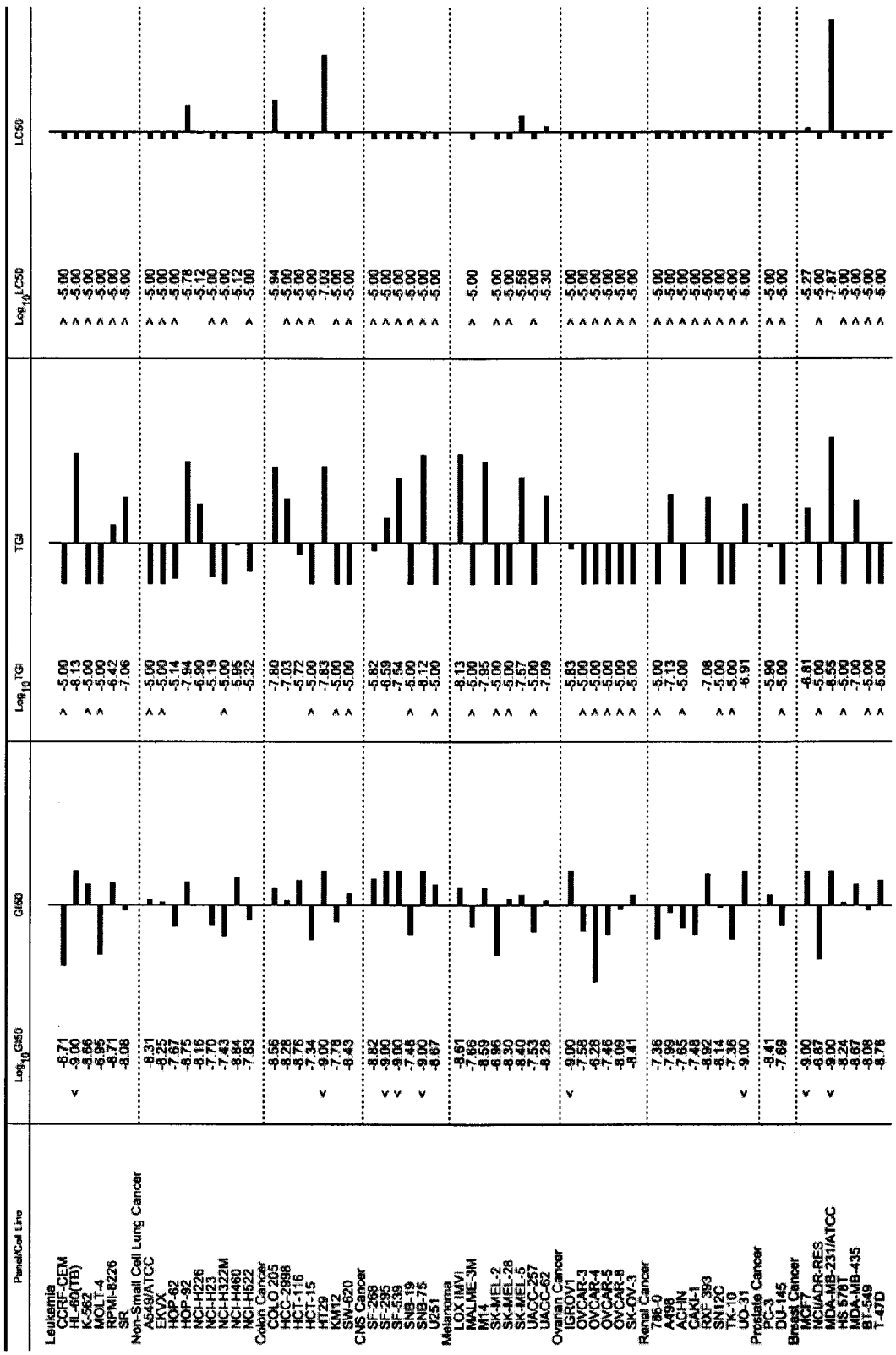

FIGS. 3A and 3B provide the $GI_{50}$ (growth inhibition of 50%), TGI (total growth inhibition), and $LC_{50}$ (lethal concentration of 50%) of coibamide A against the National Cancer Institute 60 cancer cell line panel.

Figure 4:
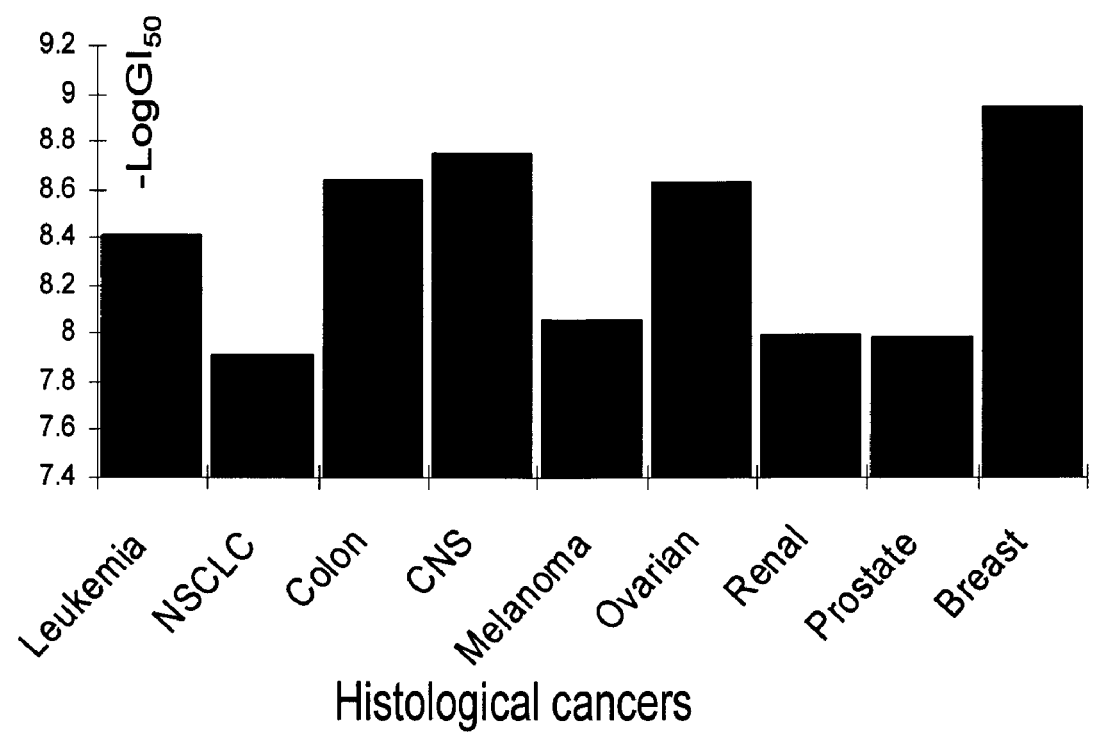

FIG. 4 provides a graphical representation of the average $-Log\ GI_{50}$ values for histological cancer types in the National Cancer Institute 60 cancer cell line panel.

Figure 5:
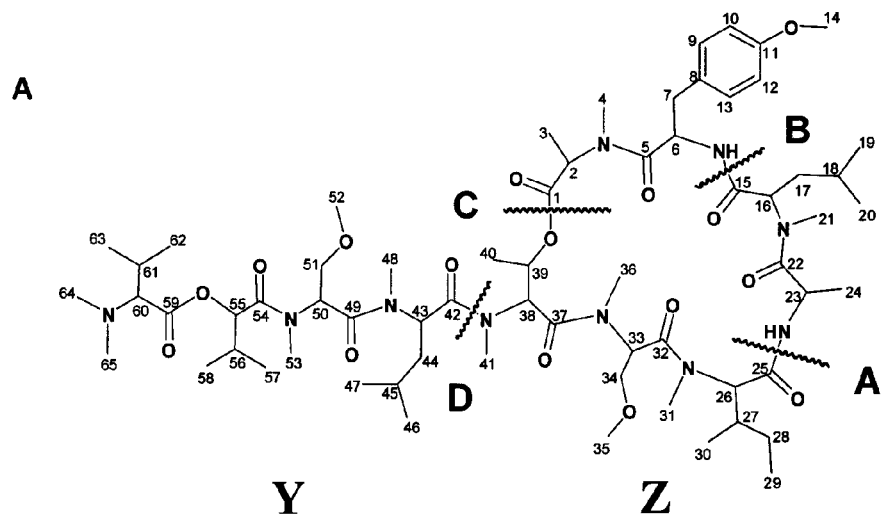
Figure 5:
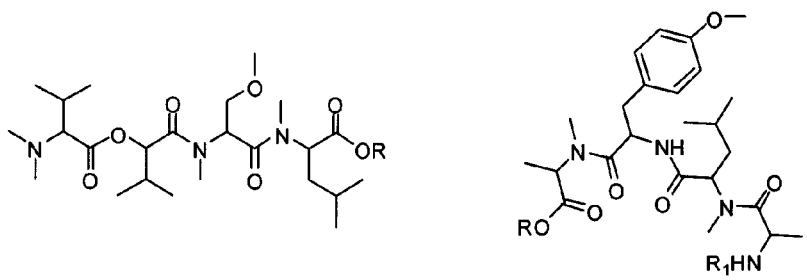
Figure 5:
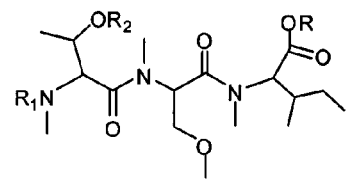
Figure 5:
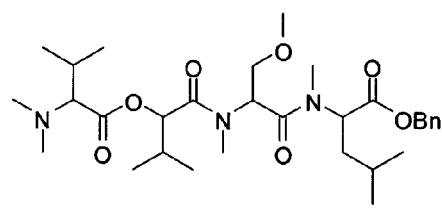

FIG. 5A provides a schematic of the disconnections proposed in the retrosynthetic analysis of the coibamide A molecule, which is partitioned into the cyclic heptadepsipeptide (Z) and the linear sidechain (Y). FIG. 5B provides a schematic of the proposed protected tri- and tetra-peptide precursors for Z. $R_1$=Ns, Boc or Fmoc and $R_2$=TBDMS or other protecting group. FIG. 5C provides an example of a side chain unit which may be coupled intact to cycle Z.

Figure 6:
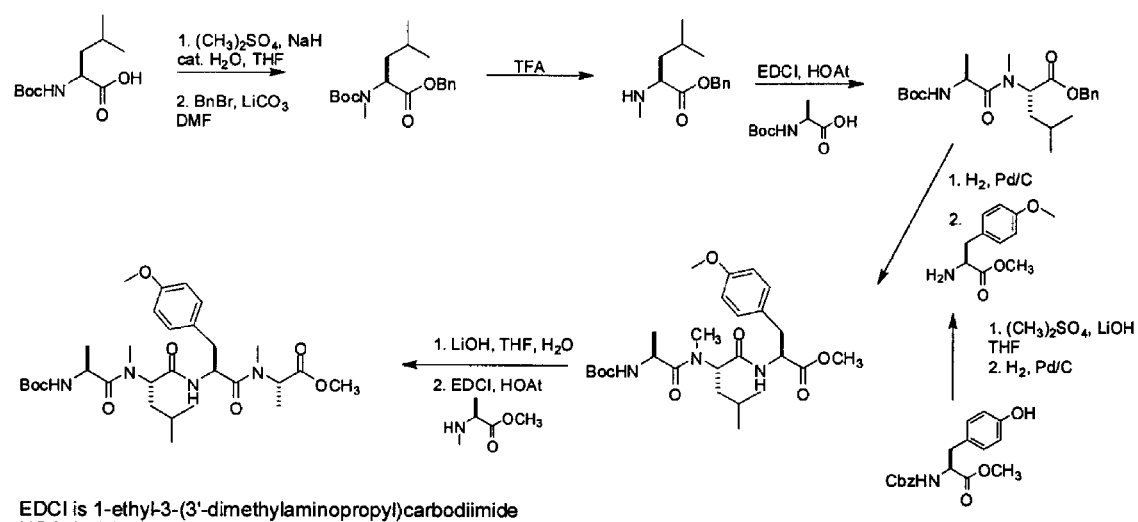

FIG. 6 provides a schematic of an example of a synthetic route to the tetrapeptide module of the cyclic heptapeptide (Z).

DETAILED DESCRIPTION OF THE INVENTION

The present invention provides new and potent antiproliferative compounds of formula (I), particularly compound 1 designated "Coibamide A". Coibamide A was isolated and wherein:
$R_1$=Me, H
$R_2$=Me, H
$R_3$=L/D N,N-dimethylvaline, L/D valine, L/D leucine, L/D isoleucine, L/D allo-isoleucine
$R_4$=O, NH, S, NMe
$R_5$=L/D 2-hydroxyisovaleric acid, L/D valine, L/D leucine, L/D isoleucine, L/D allo-isoleucine
$R_6$=H, Me
$R_7$=L/D serine, L/D O-methylserine
$R_8$=H, Me
$R_9$=L/D leucine, L/D valine, L/D isoleucine, L/D allo-isoleucine
$R_{10}$=Me, H
$R_{11}$=H, Me, $CH_3CH_2$—, $CH_3CH_2CH_2$—
$R_{12}$=O, N, S
$R_{13}$=L/D alanine
$R_{14}$=H, Me
$R_{15}$=L/D tyrosine, L/D O-methyl tyrosine, L/D phenylalanine
$R_{16}$=H, Me
$R_{17}$=L/D leucine, L/D valine, L/D isoleucine, L/D allo-isoleucine
$R_{18}$=H, Me $R_{19}$=L/D alanine
$R_{20}$=H, Me
$R_{21}$=L/D isoleucine, L/D allo-isoleucine, L/D leucine, L/D valine
$R_{22}$=H, Me
$R_{23}$=L/D serine, L/D O-methyl-serine
$R_{24}$=H, Me,
wherein $R_3$, $R_5$, $R_7$, $R_9$, $R_{13}$, $R_{15}$, $R_{17}$, $R_{19}$, $R_{21}$, $R_{23}$ are the amino acid side chains of the listed amino acids.

Modifications in the number of amino acids included in formula I are also encompassed by the instant invention. For example, the cyclic portion may be modified to contain fewer amino acids, such as 3, 4, 5, or 6 amino acids. Any of the amino acids present in the cyclic portion of the compound of formula I can be removed. When more than one amino acid is removed from formula I, the removed amino acids need not, but can be, adjacent to each other. Amino acids may also be added to the cyclic portion of formula I. For example, 1, 2, or 3 amino acids may be added to the cyclic portion such that the cyclic portion contains 8, 9, or 10 amino acid units. The added amino acid(s) can be any amino acid. When more than one amino acid is added to the cyclic portion, they can be added adjacent to each other or added to different portions of the cyclic structure.

Amino acids can be added or removed to the linear side chain of formula I. For example, 1, 2, or 3 amino acids may be added or removed from the linear side chain. Any amino acid may be added to the linear side chain and may be added at any position.

Modifications of formula I also encompass substitutions of at least one amino acid (side chain) present in formula I. In a particular embodiment, 1, 2, 3, 4, 5, 6, or 7 amino acids of formula I are substituted with another amino acid. In a another embodiment, the compounds of the instant invention have at least 75%, 80%, 85%, 90%, 95%, 97%, 99%, or 100% homology with regard to the amino acids (sequence) present in formula I. In yet another particular embodiment, the substitution is a conservative change. A conservative change is the replacement of an amino acid with one possessing similar properties, such as hydrophobicity, size, charge, polar characteristic, etc. For example, Asp and Glu are both acidic amino acids; Lys, Arg, and His are basic amino acids; Asn, Gln, Ser, Thr, and Tyr possess uncharged polar side chains; Ala, Gly, Val, Leu, Ile, Pro, Phe, Met, Trp, and Cys have nonpolar side chains; Ala, Gly, and Val are small amino acids; Val, Leu, Ile, Phe, and Tyr possess hydrophobic side chains; Phe, Tyr, and Trp possess large aromatic side chains; and Phe, Tyr, Trp, Leu, Ile, and Thr possess bulky uncharged side chains. Accordingly, the replacement of an Asp with a Glu may be considered a conservative change, but replacement of Asp with His would not be a conservative change.

The carbon that links the cyclic portion of I with the side chain can be considered the alpha carbon of an amino acid. In a particular embodiment, the amino acid can be, without limitation, L/D serine, L/D threonine, L/D allo-threonine, (2R/S)-amino-3(R/S)-hydroxypentanoic acid, or (2R/S)-amino-3(R/S)-hydroxyhexanoic acid. The amino acid selected determines $R_{11}$. While $R_{11}$ is defined in formula I as H, Me, $CH_3CH_2$—, $CH_3CH_2CH_2$—, the amino acid that forms the junction between the cyclic portion and side chain of I can also be substituted with a different amino acid, as stated hereinabove. As such, $R_{11}$ will be changed in accordance with the side chain of the substituting amino acid.

The compounds of the instant invention may have capping, protecting and/or stabilizing moieties at the N-terminus. Such moieties are well known in the art and include, without limitation, amidation. The compound may also be lipidated or glycosylated at any amino acid (i.e., a glycopeptide).

In a particular embodiment, the compound of formula I is coibamide A. Coibamide A (1) is presented below. Carbon and proton positions are designated.

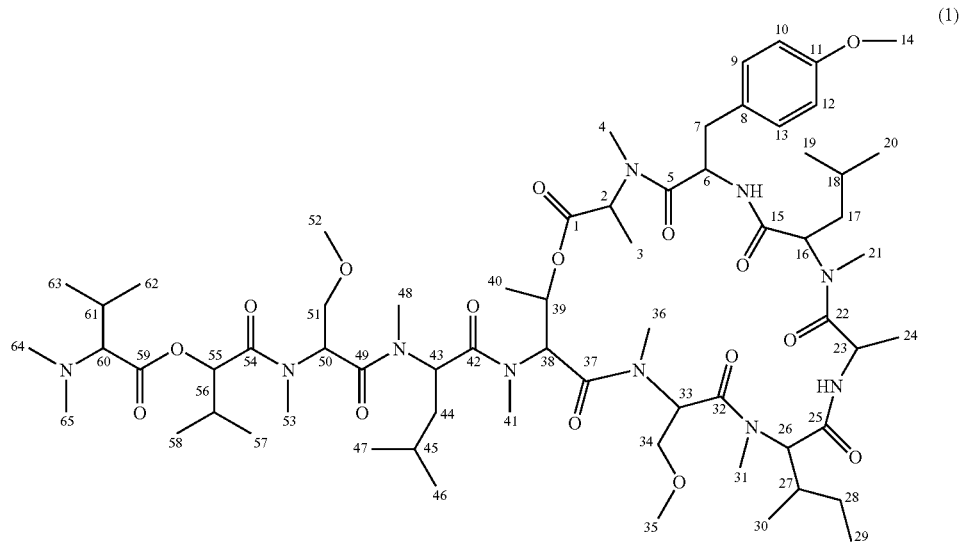

(1)

An absolute configuration of coibamide A is provided as 2.

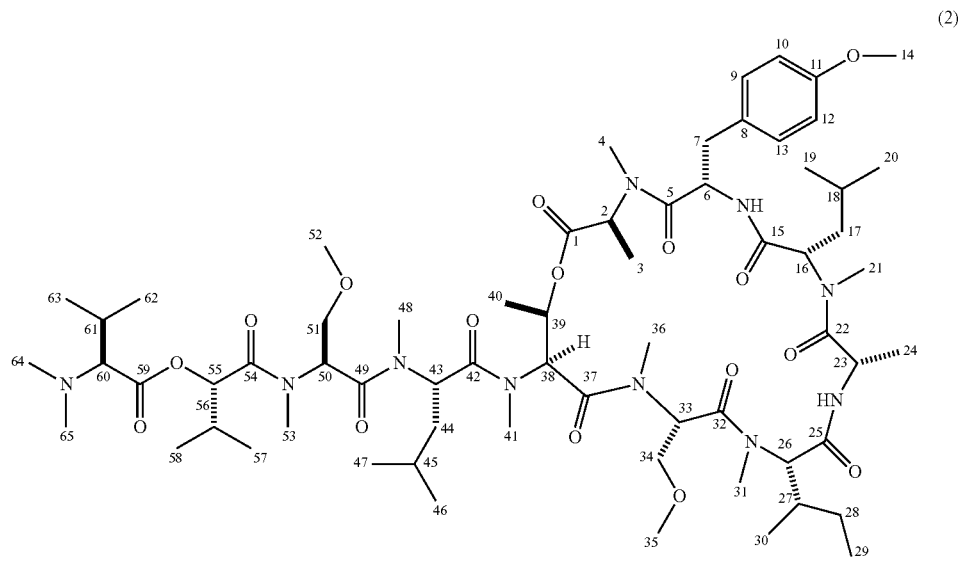

(2)

I. Definitions

The term "chemotherapeutic agent" refers generally to any compound that exhibits anticancer activity. Chemotherapeutic agents include, but are not limited to: alkylating agents (e.g., nitrogen mustards such as chlorambucil, cyclophosphamide, ifosfamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamycin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol®)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); luteinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotherapeutic agent is selected from the group consisting of: paclitaxel (Taxol®), cisplatin, docetaxel, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

A "therapeutically effective amount" of a compound or a pharmaceutical composition refers to an amount effective to prevent, inhibit, or treat the symptoms of a particular disorder or disease. For example, "therapeutically effective amount" may refer to an amount sufficient to modulate tumor growth or metastasis in an animal, especially a human, including, without limitation, decreasing tumor growth or size or preventing formation of tumor growth in an animal lacking any tumor formation prior to administration, i.e., prophylactic administration.

"Pharmaceutically acceptable" indicates approval by a regulatory agency of the Federal or a state government or listed in the U.S. Pharmacopeia or other generally recognized pharmacopeia for use in animals, and more particularly in humans.

As used herein, the term "pharmaceutically acceptable salt" is any salt that retains the activity of the parent compound. Preferably, the salt does not impart any additional deleterious or untoward effects on the subject to which it is administered compared to the parent compound. A "pharmaceutically acceptable salt" may also refer to any salt which may form in vivo as a result of administration of an acid, another salt, or a prodrug which is converted into an acid or salt.

A "carrier" refers to, for example, a diluent, adjuvant, excipient, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein, the term "amino acid" includes any one of the twenty naturally-occurring amino acids or the D-form thereof. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg), methylserine, and those provided in Table 4 of §2422 of the MPEP. Non-naturally occurring amino acids are also described in M. Bodanzsky, "Principles of Peptide Synthesis," 2nd ed., Springer-Verlag, New York, N.Y., 1993, and Stewart and Young, "Solid Phase Peptide Synthesis," 2nd ed., Pierce Chemical Co., Rockford, Ill., 1984.

As used herein, the phrase "an amino acid side chain" refers to the distinguishing substituent attached to the α-carbon of an amino acid. For example, for the amino acid glycine, the amino acid side chain is H; for the amino acid alanine, the amino acid side chain is $CH_3$, and so on.

As used herein, the term "antiproliferative" refers to activities used to, or tending to inhibit cell growth, such as antiproliferative effects on tumor cells, or antiproliferative effects on virally infected cells.

II. Therapies and Compositions

In accordance with the instant invention, compositions comprising at least one compound of formula (I) or pharmaceutically acceptable salt thereof and at least one pharmaceutically acceptable carrier are provided. The compositions may also comprise at least one other chemotherapeutic agent.

Such a pharmaceutical composition may be administered, in a therapeutically effective amount, to a patient in need thereof for the treatment of cancer. Accordingly, the present invention provides methods for the treatment of a cancer by administering to a patient, in need thereof, a therapeutically effective amount of the compounds of the instant invention, preferably in the form of a pharmaceutical composition.

As stated hereinabove, the pharmaceutical compositions of the invention may further comprise at least one chemotherapeutic agent. Suitable chemotherapeutic agents are described hereinabove. Preferred chemotherapeutic agents include, but are not limited to: paclitaxel (Taxol®), cisplatin, docetaxel, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. As an alternative, the at least one chemotherapeutic agent and the at least one compound of formula (I) may be in separate pharmaceutical compositions. In a particular embodiment of the present invention, at least one compound of formula (I) and at least one chemotherapeutic agent may be administered to the patient concurrently or sequentially. In other words, at least one compound of formula (I) may be administered first, at least one chemotherapeutic agent may be administered first, or at least one compound of formula (I) and at least one chemotherapeutic agent may be administered at the same time.

Cancers that may be treated using the present protocol include, but are not limited to: cancers of the prostate, colorectum, pancreas, cervix, stomach, colon, CNS, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell carcinoma and non-small-cell carcinoma), adrenal gland, thyroid, kidney (renal), or bone; glioblastoma, mesothelioma, neuroblastoma, renal cell carcinoma, gastric carcinoma, sarcoma, choriocarcinoma, cutaneous basocellular carcinoma, and testicular seminoma. In a particular embodiment, the cancer is selected from the group consisting of melanoma, lung (non-small-cell), leukemia, CNS, colon, renal, prostate, ovarian, and breast cancers.

The pharmaceutical compositions of the present invention can be administered by any suitable route, for example, by injection, by oral, pulmonary, nasal or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized). In a particular embodiment, the compositions of the instant invention may be administered (e.g., by injection) directly to the desired site, e.g., the tumor site.

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

The following examples are provided to illustrate various embodiments of the present invention. These examples are not intended to limit the invention in any way.

EXAMPLE 1

The marine cyanobacterium *Leptolyngbya* sp. was collected by hand using SCUBA (Jun. 26-28, 2004) from a reef pinnacle (−35 to −60 feet) off the West coast of Coiba Island (Panama) in the Coiba National Park (GPS coordinates N 07°35'08" W 081°50'30"). The collected material was stored immediately in 50% EtOH for transport, and then placed at −20° C. until further work up. The collected filamentous cyanobacterium has tentatively been assigned to the genus *Leptolynbya* (Anagnostidis et Komárek (1988) Algolog. Stud., 50-53:390).

The prokaryotic genus *Leptolyngbya* belongs to the family Oscillatoriaceae, the class Cyanophyceae and the phylum Cyanobacteria. In appearance, the *Leptolynbya* cf. cyanobacterium used herein comprised fine, clustered red filaments several centimeters in length. The thin, fine, immotile filaments (2.5-2.8 µm wide) are coiled into macroscopic clusters (several cm in diameter), with simple, thin colorless sheaths opened at the apical end; sheaths joined to the trichomes or slightly distant from them, enveloping only one, very rarely (in short sections) two trichomes. Trichomes were fine, cylindrical, and not attenuated to the ends, with rounded apical cells; not constricted at the cross walls. Cells are approximately isodiametrical or longer than wide (up to several times), cylindrical, with roughly homogeneous content, without aerotopes, rarely with scarce prominent granules; end cells without thickened cell walls or calyptras. Heterocytes and akinetes are absent.

The freshly thawed cyanobacterium (1 L wet volume) was extracted exhaustively with $CH_2Cl_2$-MeOH (2:1, 5×500 mL) and the combined organic layers were concentrated to dryness in vacuo to give 5.75 g of a dark green oil. This crude extract was fractionated by vacuum liquid chromatography (TLC grade silica gel 10-40 µm) using a stepwise gradient solvent system of increasing polarity starting from 100% hexanes to 100% MeOH. In preliminary screening, the 100% ethyl acetate fraction was cytotoxic at 300 ng/mL to NCI-H460 human lung tumor cells and was also active against malaria, leishmaniasis, and trypanosomal (*Trypanosoma cruzi*) tropical disease parasites. This fraction was separated further on a Varian Mega Bond Elute $C_{18}$ solid phase extraction cartridge (6:4 MeOH—$H_2O$) followed by reversed phase HPLC (9:1 MeOH—$H_2O$, Phenomenex Synergi Fusion 4µ, 250×10 mm column, 216 nm, 2 mL/min, $R_t$: 33.7 min) to yield coibamide A (1) as a clear oil (6.3 mg): $[\alpha]_D$ –54.1 (c 0.02, $CHCl_3$); IR (neat) 3377, 2959, 1733, 1645, 1513, 1471, 1406, 1248, 1097, 756 $cm^{-1}$. Elemental analysis (Norleu std 1.893): Tyr 1.519; Ala 2.624; MALDI-TOF MS/MS 1287.9 m/z (%) 1202.8 (26), 945.6 (6), 846.5 (8), 567.4 (28), 535.4 (9), 438.3 (24), 343.2 (19), 311.2 (10), 308.2 (4), 198.1 (12), 100.1 (100); TOF MS/MS 1287.56 ESI (positive) m/z (%) 1287.8 (42, $[M+H]^+$), 1255.8 (20), 1202.7 (28), 1184.7 (96), 1156.7 (82), 1124.7 (28), 945.6 (14), 880.6 (16), 846.5 (6), 818.5 (19), 814.5 (18), 786.5 (16), 743.4 (25), 721.5 (23), 671.4 (15), 650.4 (55), 618.4 (32), 567.3 (33), 536.2 (64), 438.2 (60), 390.2 (42), 343.2 (68), 326.2 (8), 308.8 (100), 293.2 (31), 264.2 (7), 228.1 (45), 198.1 (15), 183.2 (4), 156.1 (6), 126.1 (8), 100.1 (80); HR FT-MS obsd $[M+Na]^+$ m/z 1309.79878 (calcd for $C_{65}H_{110}O_{16}N_{10}Na$, 1309.79990); obsd $[M+H]^+$ m/z 1287.81560 (calcd for $C_{65}H_{111}O_{16}N_{10}$, 1287.818793); obsd $[M+2H]^{2+}$ m/z 644.41258 (calcd for $C_{65}H_{112}O_{16}N_{10}$, 644.41295); obsd $[M+H+NH_4]^{2+}$ m/z 652.92586 (calcd for $C_{65}H_{115}O_{16}N_{11}$, 652.92620).

NMR data for coibamide A (1) are presented in Table 1. The structure elucidation of peptide 1 by NMR spectroscopy and mass spectrometry was complicated due to its relatively high molecular weight, extensive N- and O-methylation and the presence of numerous alkyl amino acid constituents. FT-MS high resolution data for $[M+H]^+$, $[M+Na]^+$, $[M+2H]^{2+}$ and $[M+NH_4+H]^{2+}$ at m/z 1287.81560, 1309.79878, 644.41258 and 652.92586, respectively, were consistent with a molecular formula for 1 of $C_{65}H_{110}O_{16}N_{10}$. The presence of two N,O-dimethylserine residues, N-methylalanine, alanine, O-methyltyrosine, 2-hydroxy-isovaleric acid, N-methylisoleucine, two N-methylleucines and N,N-dimethylvaline was established by high field NMR experiments (Bruker DRX600 MHz spectrometer) including $^1H$-$^1H$ gCOSY, gTOCSY, gHSQC-TOCSY, multiplicity-edited gHSQC and gHMBC. These data were acquired in both deutero-chloroform and deutero-benzene. An H2BC experiment (Nyberg et al. (2005) J. Amer. Chem. Soc., 127:6154-6155) provided two bond H—C connectivities which facilitated assignment of dampened $^1H$ signals for the three leucyl residues. In addition, a $^{15}N$-gHMBC experiment, which revealed all but one of the eleven N atoms, confirmed the presence of an N,N-dimethyl moiety and aided in determining the number of amino acid residues present: information that was not discernible from the complex carbonyl region of the $^{13}C$ NMR spectrum. With ten of the eleven amino acid units in hand, and the N-terminus of the molecule defined in an N,N-dimethylvaline moiety, it remained to assign the outstanding 114 mass units ($C_5H_8O_2N$), determine the carboxyl terminus and establish the amino acid sequence in the peptide chain. Unassigned $^1H$ and $^{13}C$ signals for a methyl substituent coupled to an oxygenated methine were consistent with a lactic acid moiety. However, placement of this proposed unit as the fifth residue from the peptide N-terminus, in accordance with ROESY and HMBC data, left the carboxyl terminus undefined and 42 mass units ($C_2H_4N$) unaccounted for. In both $CDCl_3$ and $C_6D_6$, strong ROESY correlations from the methyl/oxymethine pair to an obscured broad signal ($\delta$ 2.89, 3.11 ppm, respectively) which lacked any COSY or TOCSY correlation lead to careful examination of HSQC data acquired in $C_6D_6$. These data revealed an additional heteroatom-substituted methine and in combination with variable temperature experiments allowed the assignment of an additional N-methyl substituent ($\delta_H$ 3.11, $\delta_C$ 30.6 ppm, $C_6D_6$). Hence, the remaining residue was an N-methylthreonine moiety which was linked in a cycle via an ester bond through the β-hydroxyl of its sidechain to the N-methylalanine unit six residues away. The planar structure 1 was therefore assigned to coibamide A: N,N-dimethylvalyl-hydroxyisovaleryl-N,O-dimethylseryl-N-methylleucyl-N-methylthreonyl-N,O-dimethylseryl-N-methyl-allo-isoleucyl-alanyl-N-methylleucyl-N-methyltyrosyl-N-methylalanine 1.11-3.5-lactone.

TABLE 1

$^1H$ and $^{13}C$ NMR data for coibamide A acquired in $CDCl_3$ and $C_6D_6$ (600 MHz, 298K). $^{15}N$ shifts referenced to formamide at $\delta_N$ 112.0 ppm.

| | | CDCl$_3$ | | C$_6$D$_6$ | |
|---|---|---|---|---|---|
| Unit | Atom # | $\delta_H$ (mult., J = Hz) | $\delta_C$ mult. | $\delta_H$ (mult., J = Hz) | $\delta_C$ mult. |
| N-Me-Alanine | 1 | — | 170.4$^b$ C | — | 170.9$^c$ C |
| | 2 | 5.32 (m, ob) | 51.1 CH | 5.72 (q, 7.2) | 52.1 CH |
| | 3 | 1.11 (d, 7.2) | 12.9 CH$_3$ | 1.25 (d, 7.2) | 13.7 CH$_3$ |
| | 4 | 2.35 (s) | 30.1 CH$_3$ | 2.28 (s) | 30.5 CH$_3$ |
| | N | | $\delta_N$ 115.1 | | — |
| O-Me-Tyrosine | 5 | — | 171.4$^a$ C | — | 172.6$^d$ C |
| | 6 | 5.11 (m) | 50.0 CH | 5.39 (m) | 50.7 CH |
| | 7 | 2.99 (m) 2.85 (ob) | 38.9 CH$_2$ | 3.16 (ob) 2.95 (ob) | 39.7 CH$_2$ |
| | 8 | — | 128.4 C | — | 129.6 C |
| | 9, 13 | 7.09 (d, 8.3) | 130.4 CH | 7.14 (d, 8.5) | 131.2 CH |
| | 10, 12 | 6.77 (d, 8.3) | 113.7 CH | 6.76 (d, 8.5) | 114.5 CH |
| | 11 | — | 158.6 C | — | 159.6 C |
| | 14 | 3.77 (s) | 55.3 CH$_3$ | 3.27 (s) | 55.1 CH$_3$ |
| | *NH | 6.66 (br s) | $\delta_N$ 118.2 | 6.91 (br s) | — |

TABLE 1-continued

¹H and ¹³C NMR data for coibamide A acquired in CDCl₃ and C₆D₆ (600 MHz, 298K). ¹⁵N shifts referenced to formamide at $δ_N$ 112.0 ppm.

| Unit | Atom # | CDCl₃ $δ_H$ (mult., J = Hz) | CDCl₃ $δ_C$ mult. | C₆D₆ $δ_H$ (mult., J = Hz) | C₆D₆ $δ_C$ mult. |
|---|---|---|---|---|---|
| N-Me-Leucine | 15 | — | 171.2$^a$ C | — | 170.0$^e$ C |
| | 16 | 3.62 (m, ob) | 63.6 CH | 3.34 (m, ob) | 64.1 CH |
| | 17 | 1.50 (m) | 36.1 CH₂ | 1.48 (m) | 36.9 CH₂ |
| | 18 | 1.60 (m) | 24.9 CH | 1.83 (m) | 25.7 CH |
| | 19 | 0.89 (d, 6.5) | 21.4 CH₃ | 0.72 (d, 6.4) | 21.6 CH₃ |
| | 20 | 0.94 (d, 6.5) | 23.2 CH₃ | 1.00 (d, 7.1) | 23.7 CH₃ |
| | 21 | 3.15 (s) | 39.4 CH₃ | 2.42 (s) | 39.1 CH₃ |
| | N | — | $δ_N$ 105.6 | — | — |
| Alanine | 22 | — | 171.5$^a$ C | — | 172.3$^d$ C |
| | 23 | 4.73 (br m) | 47.0 CH | 4.61 (m) | 47.9 CH |
| | 24 | 1.28 (d, 6.5) | 18.6 CH₃ | 1.03 (d, 5.5) | 19.0 CH₃ |
| | NH | 6.63 (br s) | $δ_N$ 122.4 | 6.86 (br s) | — |
| N-Me-Isoleucine | 25 | — | 167.2 C | — | 167.9 C |
| | 26 | 3.75 (m, ob) | 64.8 CH | 4.12 (m) | 65.4 CH |
| | 27 | 2.05 (m) | 32.0 CH | 2.33 (m, ob) | 33.0 CH |
| | 28 | 1.35 (m) 1.11 (ob) | 24.2 CH₂ | 1.45 (m, ob) 1.22 (m, ob) | 25.0 CH₂ |
| | 29 | 0.93 (t, ob) | 11.6 CH₃ | 0.85 (t, 7.2) | 12.1 CH₃ |
| | 30 | 0.83 (d, 6.3) | 15.7 CH₃ | 1.13 (d, 6.3) | 16.4 CH₃ |
| | 31 | 2.75 (s) | 28.9 CH₃ | 2.96 (m) | 29.4 CH₃ |
| | N | — | $δ_N$ 120.5 | — | — |
| N-Me,O-Me Serine | 32 | — | 168.7 C | — | 169.1 C |
| | 33 | 5.69 (m) | 52.8 CH | 6.07 (dd, 10.2, 4.8) | 53.6 CH |
| | 34 | 3.83 (m) 3.53 (m) | 68.6 CH₂ | 4.11 (m) 3.35 (ob) | 69.7 CH₂ |
| | 35 | 3.30 (s) | 58.8 CH₃ | 2.99 (s) | 58.9 CH₃ |
| | 36 | 2.85 (s) | 30.0 CH₃ | 3.09 (s) | 30.5 CH₃ |
| | N | — | $δ_N$ 113.4 | — | — |
| N-Me-Threonine | 37 | — | 169.7 C | — | 171.0$^c$ C |
| | 38 | 6.35 (br s) | not observed | 6.72 (ob) | 56.6 CH |
| | 39 | 5.50 (br s) | 68.0 CH | 5.96 (m) | 68.6 CH |
| | 40 | 1.07 (ob) | 18.4 CH₃ | 1.36 (d, 6.0) | 18.4 CH₃ |
| | 41 | 2.89 (br s, ob) | 29.7 CH₃ | 3.11 (s) | 30.6 CH₃ |
| | N | — | $δ_N$ 119.4 | — | — |
| N-Me-Leucine | 42 | — | 170.5$^b$ C | — | 172.2$^d$ C |
| | 43 | 5.34 (m) | 51.1 CH | 5.68 (dd, 11.4, 4.2) | 51.6 CH |
| | 44 | 1.68 (m) 1.31 (m) | 37.9 CH₂ | 1.92 (m) 1.47 (m) | 38.8 CH₂ |
| | 45 | 1.36 (m) | 25.3 CH | 1.32 (m) | 25.9 CH |
| | 46 | 0.89 (d, 6.5) | 23.1 CH₃ | 0.97 (d, ob) | 23.8 CH₃ |
| | 47 | 0.92 (d, 6.6) | 21.2 CH₃ | 0.96 (d, ob) | 21.9 CH₃ |
| | 48 | 3.13 (s) | 31.2 CH₃ | 3.55 (s) | 32.1 CH₃ |
| | N | — | $δ_N$ 117.5 | — | — |
| N-Me,O-Me Serine | 49 | — | 170.5$^b$ C | — | 171.3 C |
| | 50 | 6.02 (br s) | 52.6 CH | 6.46 (dd, 10.2, 4.3) | 53.3 CH |
| | 51 | 3.90 (m) 3.64 (dd, 11.0, 4.0) | 69.3 CH₂ | 4.16 (t, 10.6) 4.02 (dd, 11.7, 4.3) | 70.4 CH₂ |
| | 52 | 3.35 (s) | 58.6 CH₃ | 3.43 (s) | 59.0 CH₃ |
| | 53 | 3.04 (s) | 30.2 CH₃ | 2.91 (s) | 30.4 CH₃ |
| | N | — | $δ_N$ 108.5 | — | — |
| 2-hydroxyisovaleric acid | 54 | — | 170.0 C | — | 170.3$^e$ C |
| | 55 | 5.00 (d, 6.5) | 74.7 CH | 4.93 (d, 6.3) | 75.5 CH |
| | 56 | 2.21 (oct, 6.5) | 29.9 CH | 2.23 (m) | 30.6 CH |
| | 57 | 1.06 (ob) | 18.0 CH₃ | 1.10 (d, 6.8) | 18.8 CH₃ |
| | 58 | 1.06 (ob) | 18.0 CH₃ | 1.10 (d, 6.8) | 18.5 CH₃ |
| N,N-dimethyl-valine | 59 | — | 172.4 C | — | 172.5$^d$ C |
| | 60 | 2.84 (d, ob) | 73.8 CH | 2.89 (d, ob) | 74.6 CH |
| | 61 | 2.02 (m) | 27.6 CH | 2.12 (m) | 28.3 CH |
| | 62 | 0.99 (d, 6.6) | 19.5 CH₃ | 1.02 (d, 6.0) | 20.3 CH₃ |
| | 63 | 0.92 (d, 6.6) | 19.6 CH₃ | 1.04 (d, ob) | 19.9 CH₃ |
| | 64 | 2.34 (s) | 41.3 CH₃ | 2.50 (s) | 41.9 CH₃ |
| | 65 | 2.34 (s) | 41.3 CH₃ | 2.50 (s) | 41.9 CH₃ |
| | N | — | $δ_N$ 24.6 | — | — |

$^{a,b,c,d,e}$carbonyl chemical shifts are exchangeable with others of the same superscript.

As stated hereinabove, the molecular composition of 1 was established as $C_{65}H_{110}O_{16}N_{10}$ from FT-MS data ([M+H]⁺ m/z 1287.8156, Δ −2.4 mmu). The peptidic nature of 1 was evident from its complex ¹H NMR spectra in all solvents (CDCl₃, C₆D₆, DMSO, C₅D₅N). However, N-methyl conformations were minimized in CDCl₃ which showed numerous α-proton multiplets (3.62-6.02), overlapped methyl doublets (δ 0.83-1.06), mutually coupled aromatic proton doublets (δ 7.09, 6.77), a broad 2H amide proton signal (δ 6.66), and deshielded singlets integrating to 12 methyl groups attached to heteroatoms (δ 2.34-3.77).

The ¹³C NMR spectra for 1 in CDCl₃ and C₆D₆ featured an indeterminate number of resonances, with numerous ester/amide carbonyl ¹³C signals, due to localized symmetry (O-Me-Tyr, N,N-diMe-Val), steric constraints (N-Me-Thr), signal overlap and multiple conformations (in C₆D₆). These data suggested a high degree of N- and O-methylation, an observation supported by standard amino acid analysis which yielded only one alanine and one O-methyl tyrosine residue. These two amino acids, one hydroxy acid and eight N-methylated residues were assigned from 2D experiments (CDCl₃) including COSY, TOCSY, multiplicity-edited HSQC, HSQC-TOCSY, HMBC, H2BC[7] and ¹H-¹⁵N gHMBC.

Elucidation of seven of the eight N-methylated residues began with HMBC correlations from each N-methyl singlet to the corresponding α-carbon, the side-chain spin systems of which were delineated by TOCSY experiments to give N-methylalanine, two N-methylleucines, N-methylisoleucine, two N,O-dimethylserines, and an N,N-dimethylvaline residue. The latter terminal residue was described by a 6H singlet ($δ_{H-64/65}$ 2.34) that was HSQC-correlated to a prominent ¹³C resonance ($δ_{C-64/65}$ 41.3) and ¹⁵N-gHMBC-correlated to a shielded ¹⁵N resonance ($δ_N$ 24.6). Nine of ten N atoms in 1 were observed in the latter ¹⁵N-gHMBC (Martin et al. (2000) Nat. Prod., 63:543-585) experiment which showed additional correlations from five N-methyls to $δ_N$ 105.6, 108.5, 113.4, 117.5, 120.5, two α-methyls (Ala and N-Me-Ala) to $δ_N$ 115.1, 122.4, and H₂-7 of O-Me-Tyr to $δ_N$ 118.2. Hydroxyisovaleric acid (HIV) was assigned on the basis of TOCSY correlations from deshielded CH-55 ($δ_H$ 5.00, $δ_C$ 74.7) to isopropyl methine ($δ_{H-56}$ 2.21) and methyl ($δ_{H3-57/58}$ 1.06) resonances. At this point, it remained to assign 114 mass units (interpreted as $C_5H_8O_2N$=N-Me-Thr or N,O-diMe-Ser), to determine the carboxyl terminus and to establish the sequence of residues in the depsipeptide chain. COSY correlations were observed between an unassigned methyl doublet at δ 1.07 ($H_3$-40) and an oxygenated methine multiplet at δ 5.50 (H-39). Strong ROESY correlations, but no COSY or TOCSY correlations, were observed between this methyl-oxymethine pair and a very broad, partially obscured signal (δ 2.89, $CDCl_3$; 3.11 ppm, $C_6D_6$). Variable temperature experiments in $CDCl_3$ (298-328K, 700 MHz, 1 mm cryoprobe) resolved this broad peak into a 3H singlet which was HSQC-correlated to an N-methyl resonance ($δ_{C-41}$ 29.7). Furthermore, careful examination of $C_6D_6$ HSQC data revealed an additional heteroatom-substituted methine ($δ_{H-38}$ 6.72, $δ_{C-38}$ 56.6), which showed weak TOCSY correlations to the above-described methyl-oxymethine pair. Hence, the remaining residue was assigned as N-Me-Thr.

Two partial structures could be assembled based on a combination of mass spectrometric data and ROESY correlations between each N-methyl and the α-proton of the adjacent residue. Additionally, a ROESY correlation between N—$CH_3$-36 and the N-Me-Thr β- and γ-protons (H-39, $H_3$-40) positioned this residue at the N terminus of a partial structure.

A ROESY correlation between γ-$H_3$-40 of the N-Me-Thr and α-H-43 (N-Me Leu) in combination with MS fragments of m/z 535 and 567 oriented N-Me-Thr as the fifth residue in the depsipeptide backbone, thus linking the partial structures. This sequence of residues was also consistent with $MS^2$ fragments observed by LC-MS of the base hydrolysate of 1, which comprised four major linear products (3-6). Finally, an HMBC correlation from H-39 to carbonyl C-1 ($δ_C$ 170.4) indicated an ester linkage from N-Me-Thr to the C-terminal N-Me-Ala to complete the planar structure of coibamide A (1).

3

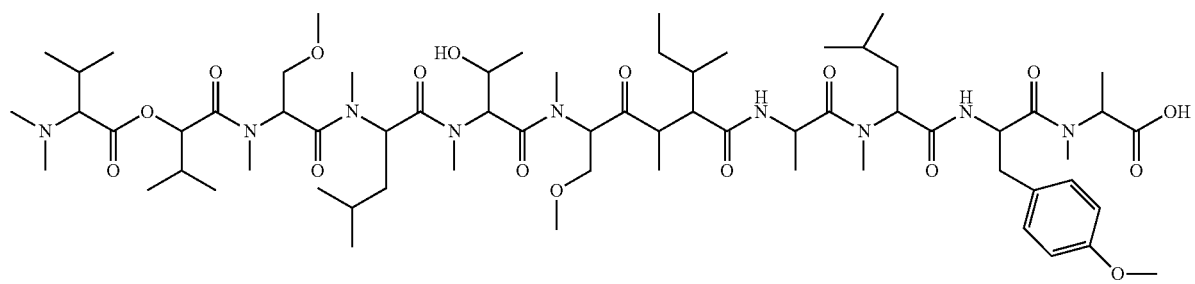

4

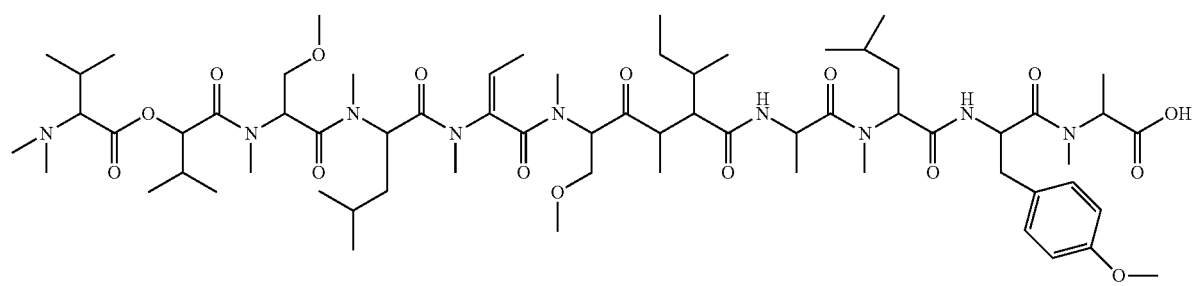

5

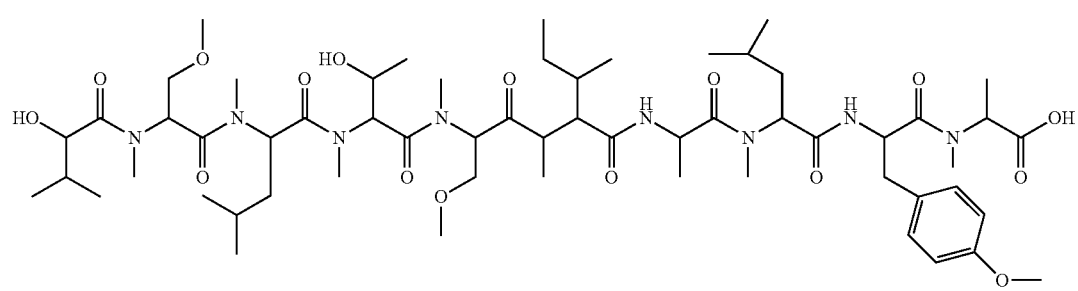

6

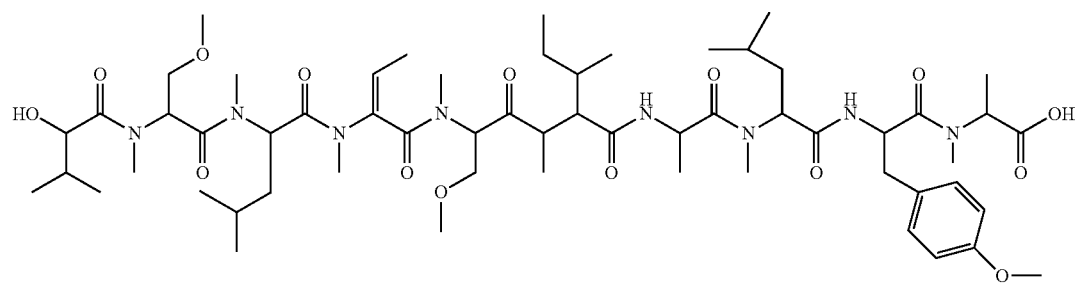

Figure 1:
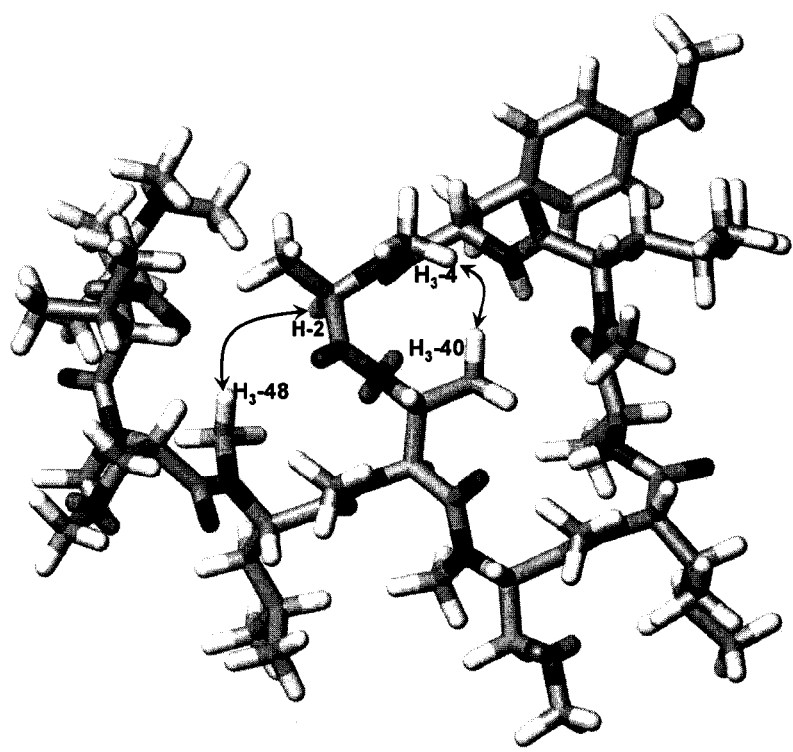
FIGS. 1A and 1B provide energy minimized computational models for coibamide A (1) containing N-Me-L-Thr (FIG. 1A) and N-Me-L-allo-Thr (FIG. 1B), with arrows indicating observed NMR ROESY correlations.
Figure 1:
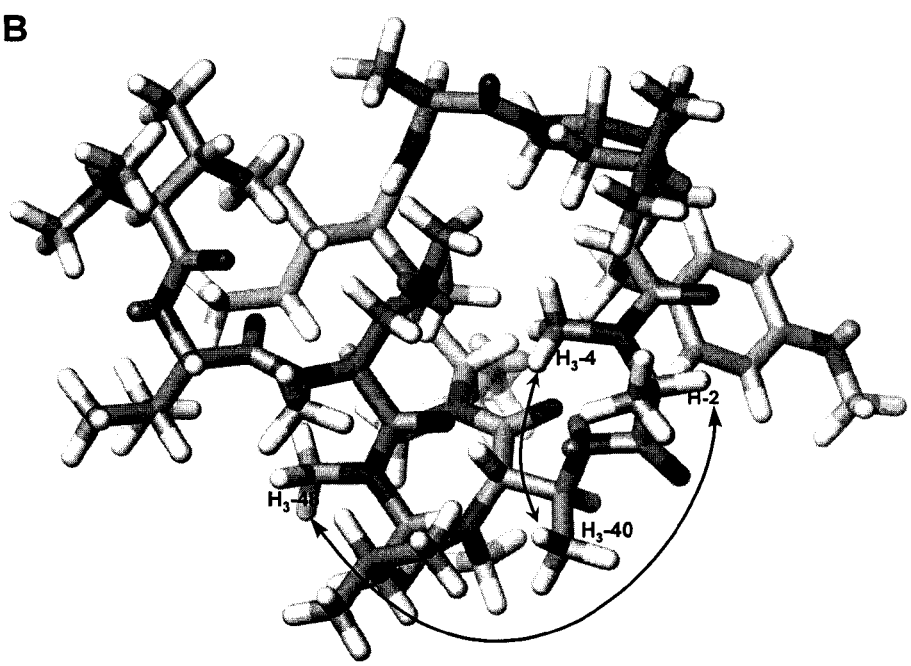

Acid hydrolysis of 1 followed by various HPLC-MS and GC-MS methodologies was used to determine the absolute configuration of coibamide A. While some standards were commercially available (N-Me-Leu, N-Me-Ile, N-Me-Ala, Ala, HIV and O-Me-Tyr), others required laboratory synthesis by standard methods (N-Me-Thr, N,N-diMe-Val, and N,O-diMe-Ser). Chiral HPLC (Phenomenex Chirex phase 3126 (D), 4.6×250 mm) established the presence of O-Me-L-Tyr, two N,O-diMe-L-Ser residues, N,N-diMe-L-Val, and L-Ala, while chiral GC-MS (CyclosilB, 30.0 m×250 μm×0.25 μm) of methylated standards and the natural product hydrolysate identified L-HIV. Treatment of the acid hydrolysate of 1 with Marfey's reagent, followed by $C_{18}$ HPLC established the presence of N-Me-L-Ile, N-Me-L-Leu, N-Me-L-Ala, and either N-Me-L-Thr or N-Me-L-allo-Thr. The presence of N-Me-L-Thr is proposed from computational models (Macromodel 9.1, FIG. 1) of the two possible coibamide structures, constrained by ROESY correlations between N—$CH_3$-4 and $CH_3$-40, and between α-H-2 and N—$CH_3$-48. NMR spectroscopy of 1 in $CDCl_3$ and $C_6D_6$ showed only one and two conformers, respectively. Thus, the extremely high degree of N-methylation appears to reduce the potential flexibility of the coibamide macrocycle in these solvents. Using Macromodel 9.1 software, each of the two coibamide isomers (model A containing N-Me-L-Thr; model B containing N-Me-L-allo-Thr; FIG. 1) was energy minimized as follows. For each model, starting bond geometries were established via a steepest descent (SD) minimization (1000 iterations, $CHCl_3$) using the MM2* force field. This was followed by a Polak-Ribier conjugate gradient (PRCG) minimization (MM2*, 10,000 iterations, $CHCl_3$) using distance constraints based on prominent ROESY correlations observed between γ-$CH_3$-40 of N-Me-Thr and $CH_3$-4 of N-Me-Ala, and α-H-2 of N-Me-Ala and N—$CH_3$-48 of the side chain N-Me-Leu. Finally, the two minimized isomers A and B, which were of similar potential energies (829 and 836 $kJmol^{-1}$), were subjected to conformational searching (1,000 step Monte Carlo, MM2*) using the same distance constraints as before to produce the final minimized models. Conformational searching applied to model B (containing N-Me-L-allo-Thr) produced lowest energy conformations which did not maintain the designated distance constraints.

EXAMPLE 2

Coibamide A displayed potent cytotoxicity to NCI-H460 lung cancer cells and neuro2a mouse blastoma cells ($LC_{50>30}$ ng/mL or 23 nM). Cytotoxicity was measured in NCI-H460 human lung tumor cells and neuro-2a mouse neuroblastoma cells using the method of Alley et. al. (Cancer Res. (1988) 48:589-601) with cell viability being determined by 3-(4,5-dimethylthiazol-2-yl)-2,5-diphenyltetrazolium bromide (MTT) reduction (Manger et al. (1995) J. AOAC Int., 78:521-527). Cells were seeded in 96-well plates at 6000 cells/well in 180 μL of RPMI 1640 medium with 10% fetal bovine serum. Twenty-four hours later, the test chemical was dissolved in DMSO, diluted into medium without fetal bovine serum and added at 20 μL/well. DMSO was less than 0.5% of the final concentration. After 48 hours, the medium was removed and cell viability determined.

Figure 2:
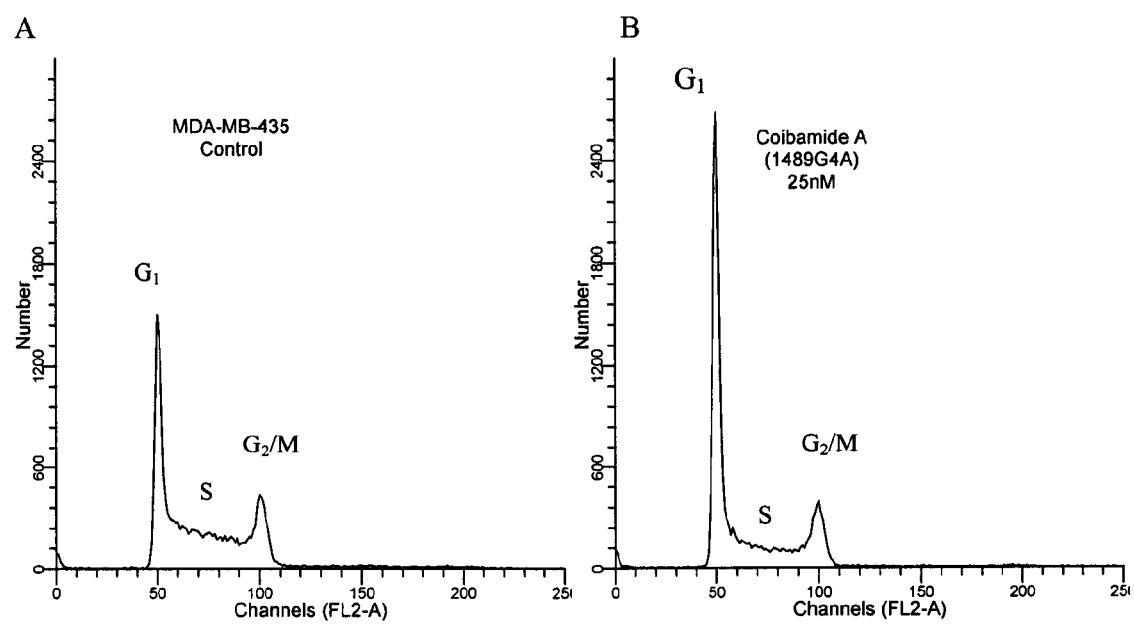
FIGS. 2A and 2B provide DNA histograms for control MDA-MB-435 cells treated with the drug vehicle (DMSO) and MDA-MB-435 cells treated with coibamide A, respectively.

Cytoskeletal assays were carried out on 1. However, immunofluorescence studies in A-10 cells did not show any of the expected microtubule changes, although some monopolar mitotic spindles were observed. Similarly, immuno-fluorescence studies in HeLa cervical cancer cells did not show any expected phenotypic effects on microtubules or on nuclear structures. At 100 nM concentration of 1 two aberrant mitotic structures were observed, and the spindles and centrosomes were normal in appearance, but the DNA alignment was not (controls were all normal). Therefore, it was hypothesized that 1 might cause mitotic abnormalities by a non-tubulin dependent mechanism, and flow cytometry studies were initiated to look at the effect of the compound on cell cycle distribution (FIG. 2). The studies showed that 1 does not cause any significant mitotic accumulation but instead causes a large increase in the number of cells in $G_1$ phase of the cell cycle with no change in $G_2$/M and a reduction of cells in S phase in a dose dependent manner.

For cell cycle analysis, MDA-MB-435 cells were treated for 24 hours with vehicle or sample. The cells were harvested and stained with Krishan's reagent. This suspension was analyzed using a Becton Dickinson FACScan flow cytometer, and the data were plotted as propidium iodide intensity versus the number of events. Quality control samples were run with each assay to ensure instrument linearity and resolution. Since cell cycle arrest in both $G_1$ and $G_2$/M is characteristic of histone deacetylase (HDAC) inhibitors, coibamide A was tested as an HDAC inhibitor, but showed no significant activity.

Coibamide A was tested against the National Cancer Institute NCI60 tumor cell lines (dtp.nci.nih.gov/branches/btb/ivclsp.html; Shoemaker, R. H. (2006) Nat. Rev. Cancer, 6:813-823), which comprises 60 human cancer cell lines including leukemias, melanomas, ovarian, renal, prostate, breast, colon, lung and central nervous system (CNS) cancers (the data from two screens are provided in FIGS. 3A and 3B). All test compounds are evaluated against the 60 cell lines at a single dose (10 μm for coibamide A) and those which exhibit significant growth inhibition are then evaluated against the 60 cell panel at five concentration levels to generate three dose response parameters for each test compound. Growth inhibition of 50% ($GI_{50}$) is the drug concentration resulting in a 50% reduction in the net protein increase in control cells during the drug incubation. Similarly, total growth inhibition (TGI) is the drug concentration resulting in zero net protein increase in control cells, and the lethal concentration of 50% ($LC_{50}$) is the drug concentration resulting in a 50% reduction in the measured protein at the end of the drug treatment as compared to that at the beginning, (a net loss of cells following treatment). Preliminary results for coibamide A show that it has significant antiproliferative activity. Coibamide A produced mean cytostatic ($GI_{50}$ and TGI with range) and cytotoxic ($LC_{50}$ and range) parameters as follows: log $GI_{50}$, −8.04 (2.96); log TGI, −5.85 (3.43); log $LC_{50}$, −5.11 (2.66). These log mean values of <−4 with log range values of >2 indicate both potency and histological selectivity (FIG. 4).

Nanomolar or better $GI_{50}$ values were observed for coibamide A against 53 of the 55 cancer cell lines screened, with undefined activities (<1 nM) for two colon cancer (HCC-2998 and HT29), one melanoma (SK-MEL-5) and one breast cancer (T-47D) cell line. From the mean graph for $GI_{50}$ values, coibamide A was consistently active against leukemias, CNS, colon, and breast cancer cells. $GI_{50}$ values for coibamide activity against melanoma and prostate cancer cell lines were distributed approximately equally above and below the mean showing no generalized trend for those cancer lines tested. Total growth inhibition parameters (TGI) for coibamide A confirmed a general inhibition of CNS cancer cell lines, but also revealed potent selective cytotoxicity that was three to four orders of magnitude greater for particular cell lines distributed through several cancer types. The mean graph for TGI values for coibamide A shows potent antiproliferative activity to the following 12 cell lines: SR (leukemia, 16.6 nM), HOP-92 (NSCLC, 25.4 nM), COLO 205 (colon cancer, 4.9 nM), HCC-2998 (colon cancer, 8.3 nM), HT29 (colon cancer, 10.4 nM), SF-295 (CNS cancer, 21.9 nM), SF-539 (CNS cancer, 30.3 nM), LOX IMVI (melanoma, 6.6 nM), SK-MEL-5 (melanoma, 6.0 nM), SK-OV-3 (ovarian cancer, 9.8 nM), MDA-MB-231/ATCC (breast cancer, 25.1 nM) and T-47D (breast cancer, 5.4 nM). Comparable results were evident in the mean graph of TGI values for coibamide A from a second screen: HL60(TB) (leukemia, 7.4 nM), SR (leukemia, 87.0 nM), HOP-92 (NSCLC, 11.4 nM), COLO 205 (colon cancer, 15.7 nM), HCC-2998 (colon cancer, 93.7 nM), HT29 (colon cancer, 14.6 nM), SF-539 (CNS cancer, 28.7 nM), SNB-75 (CNS cancer 7.6 nM), LOX IMVI (melanoma, 7.4 nM), M-14 (melanoma, 11.2 nM), SK-MEL-5 (melanoma, 26.9 nM), UACC-62 (renal cancer, 80.6 nM), A498 (renal cancer, 74.4 nM), RXF 393 (renal cancer, 82.3 nM), MDA-MB-231/ATCC (breast cancer, 2.8 nM) and MDA-MB-435 (breast cancer, 100 nM). Interestingly, coibamide A was most potently cytotoxic to COLO 205 and HT29 colon cancer cells ($LC_{50}$ 35.8 nM and 93.3, respectively).

Results of particular interest include the potent antiproliferative activity of coibamide A against aggressive tumor types such as melanoma and CNS tumors. These types of tumors are notoriously difficult to inhibit in vivo. Considering the TGI of the breast cancer cell lines, it is remarkable that the two highly sensitive cell lines have very different cellular characteristics. The MDA-MB-231 breast cancer cell line is one of the most sensitive cell lines, and is very rapidly growing, highly metastatic, p53 mutant and estrogen receptor (ER) negative. In contrast, the T47D cell line is ER positive, non-invasive and non-tumorigenic. Furthermore, there appears to be no dependence on p53 status of cell line sensitivity to coibamide A. The sensitive SR leukemia cell line is p53 wildtype, while the sensitive NSCLC cell line has mutant p53. Of the two CNS cell lines one is p53 mutant and one p53 wildtype. Interestingly all of the sensitive melanoma cell lines have wildtype p53, which is most common for melanoma since they show INK4 pathway defects.

Most of the cell lines in the NCI panel responded to coibamide A in a cytostatic manner (dose response curves level off as concentration increases), with the exception of the 12 mentioned above in which 1 causes significant cytotoxicity (TGI). It is therefore evident that coibamide A and compounds of formula I will have good selectivity for particular cancer cell types over normal cells. Intriguingly, the biological response pattern of coibamide A in the NCI60 panel is unlike any compound in the NCI "Standard Agent Database" or in the full NCI database which includes crude extracts and fractions. This comparison is performed by the NCI using the COMPARE algorithm. (dtp.nci.nih.gov/docs/compare/compare.html). Therefore, based on the preliminary NCI data, coibamide A has been designated COMPARE negative: the pattern of cell line sensitivity does not match, in a significant way, patterns of any compounds of known mechanism.

EXAMPLE 3

The peptidic molecular structure of coibamide A presents a large number of possible combinations and permutations of component amino acid residues for structure activity relationship studies and/or drug development (e.g., increase bioavailability and/or decrease toxicity). Coibamide A and many of its analogs are accessible through a modular convergent synthetic strategy which is summarized below. This flexible approach permits the exchange of individual amino acids in one module without affecting the other modules, and also provides access to truncated analogs.

The cyclic heptadepsipeptide portion (Z) of coibamide A (FIG. 5A) can be constructed from appropriately protected N,O-dimethylthreonine-O-methylserine-N-methylisoleucine, O-methyltyrosine-N-methylalanine and alanine-N-methylleucine. The tripeptide and tetrapeptide can each be prepared separately (FIG. 5B) before being coupled to form the cycle. Disconnections A (or B) are preferred for final ring closure since the ester bond (C) should be formed less readily due to the poorer nucleophilicity of oxygen versus nitrogen.

The side chain (Y) can be assembled intact as protected N,N-diMe-Val-HIV-N,O-diMeSer-N-Me-Leu benzyl ester (FIG. 5C) and then condensed with the threonine nitrogen to form coibamide A (connection D; FIG. 5A). As an alternative (e.g., if there is interference from the N,N-dimethylvaline tertiary amine), then the side chain can be added stepwise.

Solution phase or solid phase techniques may be used to synthesize the precursor oligopeptides (FIG. 6).

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated compound of formula I or a pharmaceutically acceptable salt thereof,

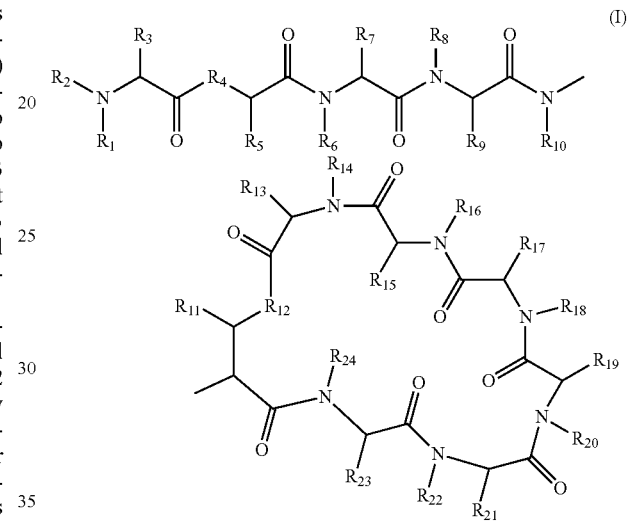

wherein:
$R_1$=Me or H;
$R_2$=Me or H;
$R_3$=L/D N,N-dimethylvaline, L/D valine, L/D leucine, L/D isoleucine, or L/D allo-isoleucine;
$R_4$=O, NH, S, or NMe;
$R_5$=L/D 2-hydroxyisovaleric acid, L/D valine, L/D leucine, L/D isoleucine, or L/D allo-isoleucine;
$R_6$=H or Me;
$R_7$=L/D serine or L/D O-methylserine;
$R_8$=H or Me;
$R_9$=L/D leucine, L/D valine, L/D isoleucine, or L/D allo-isoleucine;
$R_{10}$=Me or H;
$R_{11}$=H, Me, $CH_3CH_2$—, or $CH_3CH_2CH_2$—;
$R_{12}$=O, N, or S;
$R_{13}$=L/D alanine;
$R_{14}$=H or Me;
$R_{15}$=L/D tyrosine, L/D O-methyl tyrosine, or L/D phenylalanine;
$R_{16}$=H or Me;
$R_{17}$=L/D leucine, L/D valine, L/D isoleucine, or L/D allo-isoleucine;
$R_{18}$=H or Me;
$R_{19}$=L/D alanine;
$R_{20}$=H or Me;
$R_{21}$=L/D isoleucine, L/D allo-isoleucine, L/D leucine, or L/D valine;
$R_{22}$=H or Me;
$R_{23}$=L/D serine or L/D O-methyl-serine; and
$R_{24}$=H or Me,
wherein $R_3$, $R_5$, $R_7$, $R_9$, $R_{13}$, $R_{15}$, $R_{17}$, $R_{19}$, $R_{21}$, and $R_{23}$ are the amino acid side chains of the listed amino acids.

2. The compound of claim 1, wherein the compound is:
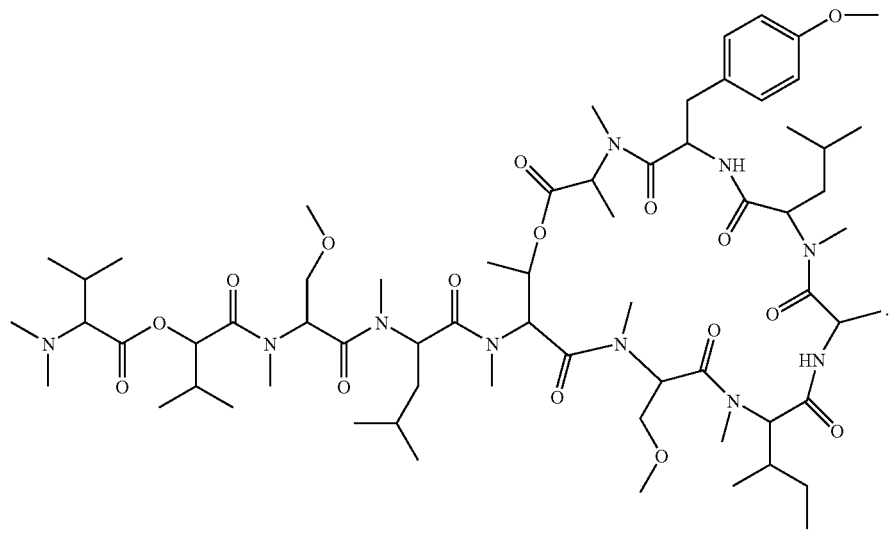
3. A composition comprising at least one compound of claim 1 and at least one pharmaceutically acceptable carrier.
4. The composition of claim 3, further comprising at least one chemotherapeutic agent.
* * * * *